(12) United States Patent
Mirov et al.

(10) Patent No.: US 9,295,403 B1
(45) Date of Patent: Mar. 29, 2016

(54) MULTIPURPOSE WEARABLE ELECTRICAL CONTACT

(71) Applicant: Verily Life Sciences LLC, Mountain View, CA (US)

(72) Inventors: Russell Norman Mirov, Los Altos, CA (US); John Lapetina, Los Altos Hills, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 59 days.

(21) Appl. No.: 14/135,246

(22) Filed: Dec. 19, 2013

(51) Int. Cl.
*A61B 5/0492* (2006.01)
*A61B 5/053* (2006.01)
*A61B 5/00* (2006.01)

(52) U.S. Cl.
CPC ............. *A61B 5/0533* (2013.01); *A61B 5/0004* (2013.01); *A61B 5/0492* (2013.01); *A61B 5/681* (2013.01); *A61B 5/6824* (2013.01); *A61B 5/7435* (2013.01)

(58) Field of Classification Search
CPC ...... A61B 5/0492; A61B 5/033; A61B 5/681; A61B 5/6824
USPC .................................................. 600/390, 547
See application file for complete search history.

(56) References Cited

U.S. PATENT DOCUMENTS

| | | | |
|---|---|---|---|
| 6,238,338 B1 * | 5/2001 | DeLuca et al. ................ | 600/300 |
| 6,881,191 B2 * | 4/2005 | Oakley et al. ................. | 600/483 |
| 8,352,012 B2 * | 1/2013 | Besio ............................. | 600/388 |
| 8,364,250 B2 | 1/2013 | Moon et al. | |
| 8,444,578 B2 | 5/2013 | Bourget et al. | |
| 2010/0312188 A1 * | 12/2010 | Robertson et al. ............ | 604/156 |
| 2012/0245439 A1 | 9/2012 | Andre et al. | |
| 2013/0053661 A1 | 2/2013 | Alberth et al. | |
| 2013/0231574 A1 | 9/2013 | Tran | |

OTHER PUBLICATIONS

Micah Abrams, "Basis B1 Review," Digital Trends Reviews, Jun. 29, 2013.

* cited by examiner

*Primary Examiner* — Lee S Cohen
(74) *Attorney, Agent, or Firm* — McDonnell Boehnen Hulbert & Berghoff LLP

(57) ABSTRACT

Wearable devices are described herein including a housing and a mount configured to mount the housing to an external surface of a wearer. The wearable devices further include first and second electrical contacts protruding from the housing and configured such that the electrical contacts can be used to measure a Galvanic skin resistance of skin proximate to the electrical contacts when the wearable device is mounted to the external surface of the wearer. The wearable devices are powered by rechargeable batteries disposed within the wearable devices. The electrical contacts are additionally configured to connect the wearable device to an external charger or other power source such that a recharger disposed within the wearable device can recharge the rechargeable battery using power from the external charger or other power source.

18 Claims, 11 Drawing Sheets

MULTIPURPOSE WEARABLE ELECTRICAL CONTACT

BACKGROUND

Unless otherwise indicated herein, the materials described in this section are not prior art to the claims in this application and are not admitted to be prior art by inclusion in this section.

The Galvanic skin response is a change in the conductivity and/or electrical potential of the skin due to changes in the moisture level of the skin. This change in moisture level can be caused by activation or inactivation of sweat glands in the skin. The Galvanic skin response includes the Galvanic skin resistance (GSR), a measure of the conductivity of the skin between two or more points, and the Galvanic skin potential (GSP), a measure of the voltage difference between two or more points on the skin.

SUMMARY

Some embodiments of the present disclosure provide a wearable device, including: a housing; a rechargeable battery disposed within the wearable device; a mount configured to mount the housing to an external body surface; first and second electrical contacts protruding from the housing, wherein the first and second electrical contacts are configured to contact skin at the external body surface when the housing is mounted on the external body surface such that a Galvanic skin resistance (GSR) of the skin at the external body surface can be measured between the first and second electrical contacts; and electronics disposed in the wearable device. The electronics disposed in the wearable device include: a recharger configured to recharge the rechargeable battery, wherein the recharger is configured to be powered through the first and second electrical contacts; and a GSR sensor configured to obtain a measurement relating to the GSR of the skin at the external body surface, via the first and second electrical contacts, when the recharger is not being powered through the first and second electrical contacts.

Some embodiments of the present disclosure present a method, including: charging a wearable device, wherein the wearable device comprises: (i) a housing, (ii) a rechargeable battery disposed within the wearable device, (iii) a mount configured to mount the housing to an external body surface, (iv) first and second electrical contacts protruding from the housing, (v) a GSR sensor configured to obtain a measurement relating to a GSR of skin via the first and second electrical contacts, (vi) a recharger configured to recharge the rechargeable battery, wherein the recharger is configured to be powered through the first and second electrical contacts, and (vii) a rectifier connected between the recharger and the first electrical contact, wherein the rectifier is configured to be forward biased when the recharger is being powered through the first and second electrical contacts and reverse biased when the recharger is not being powered through the first and second electrical contacts, wherein charging the wearable device comprises powering the recharger through the first and second electrical contacts; mounting the wearable device to an external body surface using the mount, wherein mounting the wearable device to an external body surface comprises mounting the housing to the external body surface using the mount such that the first and second electrical contacts contact skin at the external body surface-such that a Galvanic skin resistance (GSR) of the skin at the external body surface can be measured between the first and second electrical contacts; obtaining a measurement using the GSR sensor while the rectifier is reverse biased; and determining a GSR of the skin at the external body surface based on the measurement obtained using the GSR sensor.

These as well as other aspects, advantages, and alternatives, will become apparent to those of ordinary skill in the art by reading the following detailed description, with reference where appropriate to the accompanying drawings.

DETAILED DESCRIPTION

Figure 1:
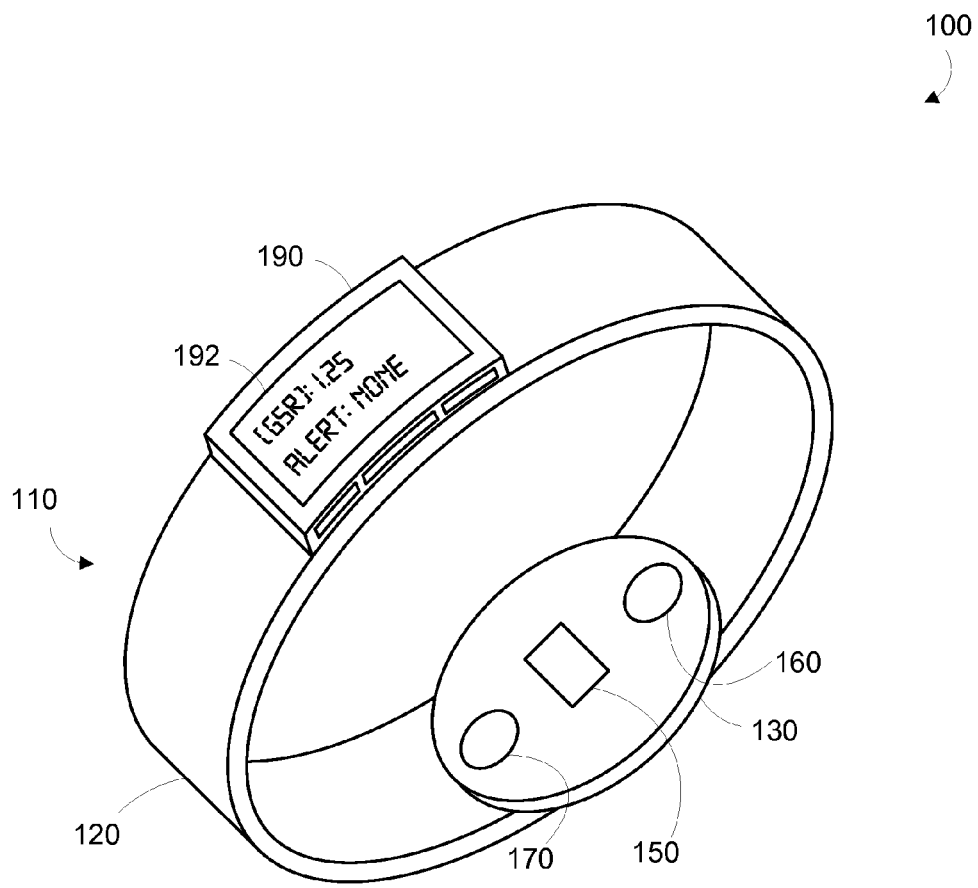
FIG. 1 is a perspective view of an example wearable device.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

I. Overview

A wearable device may be configured to measure one or more physiological parameters of the wearer. The one or more physiological parameters can include Galvanic skin resistance, which may be related to perspiration and, thus, the wearer's activity level, sympathetic nervous system activity, and/or emotional state/affect. To measure Galvanic skin resistance, the wearable device may include two electrical contacts that protrude from a housing of the device so as to contact the wearer's skin at a location such as the wearer's wrist, forearm, upper arm, leg, thigh, etc. With the electrical contacts against the wearer's skin, electronics within the device may be used to measure an external resistance between the first and second electrical contacts. This external resistance is related to the wearer's Galvanic skin resistance. The electronics may be powered by a rechargeable battery in the wearable device. The wearable device may further include a recharger for recharging the rechargeable battery. To recharge the rechargeable battery, the recharger may be connected to an external power source through the first and second electrical contacts.

In some examples, the wearable device includes a housing (e.g., a water-resistant housing) and a mount (e.g., a band) that can mount the housing on a particular external body location, such as a wrist. The first and second electrical contacts may protrude from a side of the housing facing the skin at the body location, such that the first and second electrical contacts contact the skin when the housing is mounted on the body location. Electronics disposed in the housing may include a GSR sensor configured to obtain a measurement relating to the GSR of the skin at the external body surface, via the first and second electrical contacts, when a rectifier included in the electronics is reverse biased.

In some examples, the GSR sensor includes a reference voltage source configured to provide a reference voltage (relative to the second electrical contact) and a resistor (having a reference resistance) connected between the reference voltage source and first electrical contact. In this way, the reference resistance of the resistor and the external resistance between the first and second electrical contacts may act as a voltage divider, such that a fraction of the reference voltage appears across the first and second electrical contacts; the fraction is related to the external resistance and the reference resistance. The electronics in the housing may further include a voltage sensor configured to sense the fraction of the reference voltage between the first and second electrical contacts. In one example, the voltage sensor includes an operational amplifier configured as a voltage follower and an analog-to-digital converter that provides a digital output representative of the voltage from the operational amplifier.

The electronics in the housing may include the recharger and a rectifier (e.g., a diode) connected between the recharger and the first electrical contact. The rectifier is configured to be forward biased when the recharger is being powered through the first and second electrical contacts and reverse biased when the recharger is not being powered through the first and second electrical contacts. In this way, when the recharger is not being powered through the first and second electrical contacts, the recharger is electrically isolated from the reference voltage source, resistor, electrical contacts, and voltage sensor (except possibly for a small leakage current through the rectifier).

In some examples, the wearable device may include a user interface that is configured to provide user-discernible indications (e.g., visual, audible, and/or tactile indications) of one or more physiological parameters measured and/or determined by the device, such as Galvanic skin resistance. In some examples, the wearable device may include a wireless communication interface that can transmit data to an external device, for example, using Bluetooth, ZigBee, WiFi, and/or some other wireless communication protocol. The data transmitted by the wireless communication interface may include data indicative of one or more physiological parameters measured by the device, such as Galvanic skin resistance.

II. Example Wearable Devices

A wearable device 100 can be configured to measure a Galvanic skin resistance (GSR) of skin at an external body surface proximate to the wearable device 100. The wearable device 100 can also be configured to be powered by a rechargeable battery disposed in the wearable device 100. The term "wearable device," as used in this disclosure, refers to any device that is capable of being worn at, on or in proximity to an external body surface, such as a wrist, ankle, waist, chest, or other body part. A mount 110, such as a belt, wristband, ankle band, etc. can be provided to mount the device at, on or in proximity to the external body surface. In some embodiments, a mount could additionally or alternatively include an adhesive. For example, a mount could include and adhesive and could be configured such that it could be used to mount a wearable device to an external body surface of a wearer without wrapping around a part of the wearer (e.g., a limb). The mount 110 may prevent the wearable device 100 from moving relative to the body to ensure consistent contact between the wearable device 100 and the skin to enable consistent measurement of the GSR of the skin. In one example, shown in FIG. 1, the mount 110, may take the form of a strap or band 120 that can be worn around a part of the body.

A housing 130 is disposed on the mount 110 such that the housing 130 can be positioned on an external surface of the body. In this position, a first electrical contact 160 and a second 170 electrical contact protruding from the housing 130 could contact skin at the external surface of the body such that the GSR of the skin at the external surface of the body could be measured between the first and second electrical contacts 160, 170. The first and second electrical contacts 160, 170 could be configured to interface with a charger or other device such that a rechargeable battery that powers the wearable device 100 could be charged through the first and second electrical contacts 160, 170.

The first and second electrical contacts 160, 170 could be composed of an electrically conductive material, such as a metal or a combination of metals, or a nonmetal conductor. The first electrical contact 160 and second electrical contact 170 could be composed of the same material or different materials. The first and second electrical contacts 160, 170 could each be composed of a single material or could be composed of multiple materials. For example, the electrical contacts 160, 170 could have a bulk composed of one material and a surface plating of another material. For example, the electrical contacts 160, 170, could have a bulk composed of copper and a surface composed of gold or of gold alloyed with nickel and/or cobalt. The surface layer could be deposited by a number of methods familiar to one skilled in the art; for example, electroplating. Other compositions are possible, as well.

The first and second electrical contacts 160, 170 could be spring loaded. That is, the electrical contacts 160, 170 could be configured to include one or more springs or other elements that could be reversibly compressed. The electrical contacts 160, 170 could be spring loaded in a direction perpendicular to an external surface of the body to which the housing 130 could be mounted. That is, the electrical contacts 160, 170 could be spring loaded in order to improve and/or make more consistent an electrical connection between the electrical contacts 160, 170 and skin of the external body surface to which the housing 130 was mounted by the mount 110. Alternatively, first and second electrical contacts 160, 170 could be fixed relative to housing 130.

The geometry of the aspects of the electrical contacts 160, 170 that protrude from the housing 130 could be configured to improve and/or make more consistent an electrical connection between the electrical contacts 160, 170 and skin of the external body surface to which the housing 130 was mounted by the mount 110. For example, the protruding aspects of the electrical contacts 160, 170 could be hemispherical, conical, parabolic, cylindrical, or shaped in some other manner. The electrical contacts 160, 170 could be flat or substantially flat plates (e.g., rectangular, triangular, or other-shaped plates protruding from the housing 130). The electrical contacts 160, 170 could have a faceted geometry. For example, the electrical contacts 160, 170 could be triangular, rectangular, or other-shapes pyramids. The protruding aspects of the electrical contacts 160, 170 could have, for example, a characteristic size (e.g., diameter of cylinders, cones, or hemispheres, width of rectangular prisms or plates, or some other measure of size) between 1 and 5 millimeters. Further, the protruding aspects of the electrical contacts 160, 170 could have an inscribed, cast, and/or pressed texture or pattern. Additionally or alternatively, the exposed aspects of the electrical contacts 160, 170 could be roughened mechanically, chemically, or by some other method. Other geometries, sizes, surface treatments, and other aspects of the configuration of the electrical contacts 160, 170 are anticipated.

The electrical contacts 160, 170 could be arranged a distance apart such that a GSR measured using the electrical contacts 160, 170 could have a desired property or properties. For example, the electrical contacts 160, 170 could be separated by a distance of between 1 and 50 millimeters, such as about 25 millimeters. The electrical contacts 160, 170 could be disposed on the housing 130 such that, if the housing 130 is mounted to a wrist of a wearer of the wearable device 100, the electrical contacts 160, 170 would be arranged on a line substantially parallel to the bones of the forearm of the wearer (i.e., the humerus and ulna). Other distances and directions are also possible.

The housing 130 could be configured to be water-resistant. That is, the housing could be configured to include sealants, adhesives, gaskets, welds, press-fitted seams, and/or other joints such that the housing 130 was resistant to water entering an internal volume or volumes of the housing 130. Further, the interface between the housing 130 and the first and second electrical contacts 160, 170 protruding from the housing 130 could be configured such that the combination of the housing 130 and the electrical contacts 160, 170 is water-resistant.

The wearable device 100 includes electronics (not shown in FIG. 1) configured to measure a Galvanic skin resistance (GSR) of the skin at an external surface of the body proximate to the housing 130, using the first and second electrical contacts 160, 170 when the wearable device 100 is mounted to the external surface of the body. The electronics may include a GSR sensor configured to obtain a measurement relating to the GSR of the skin at the external surface of the body, via the first and second electrical contacts 160, 170, when a rectifier disposed in the wearable device 100 is reverse biased. The GSR sensor could include a reference voltage source electrically connected to the first electrical contact 160 through a resistor having a reference resistance. The GSR sensor may also include a voltage sensor electrically connected to the first electrical contact 160. The reference voltage source generates a reference voltage relative to the second electrical contact 170 and the voltage sensor measures a voltage between the first electrical contact 160 and the second electrical contact 170. A battery recharger could also be included in the electronics and electrically connected to the first electrical contact 160 through the rectifier.

A GSR of skin proximate to the electrical contacts 160, 170 could be determined based on a measurement relating to the GSR of the skin obtained using the GSR sensor when the wearable device 100 is mounted to the external surface of the body and when the rectifier is reverse biased. In some examples, the measurement relating to the GSR of the skin could include a measurement of the voltage between the first and second electrical contacts 160, 170, and the GSR of skin proximate to the electrical contacts 160, 170 could be determined based on the measured voltage, the value of a reference voltage produced by a reference voltage source, a resistance of a reference resistor, and/or other factors. For example, the GSR could be determined by calculating a multiple of the reference resistance corresponding to the measured voltage divided by a difference, where the difference is the measured voltage subtracted from the reference voltage. Other methods of determining a GSR could be used, for example a lookup table relating measured voltages to GSR values.

The electrical contacts 160, 170 protruding from the housing 130 could additionally be used for other purposes. For example, electronics disposed in the wearable device 100 could be used to sense an electrocardiogram (ECG) signal, a Galvanic skin potential (GSP), an electromyogram (EMG) signal, and/or some other physiological signal present at the electrical contacts 160, 170. Additionally or alternatively, the electrical contacts 160, 170 could be used to detect the presence of a charging device or some other electronic system electrically connected to the electrical contacts 160, 170.

In some examples, the housing 130 further includes at least one detector 150 for detecting at least one other physiological parameter, which could include any parameters that may relate to the health of the person wearing the wearable device. For example, the detector 150 could be configured to measure blood pressure, pulse rate, respiration rate, skin temperature, etc. At least one of the detectors 150 could be configured to non-invasively measure one or more targets in blood circulating in subsurface vasculature proximate to the wearable device. In a non-exhaustive list, detector 150 may include any one of an optical (e.g., CMOS, CCD, photodiode), acoustic (e.g., piezoelectric, piezoceramic), electrochemical (voltage, impedance), thermal, mechanical (e.g., pressure, strain), magnetic, or electromagnetic (e.g., RF, magnetic resonance) sensor.

The wearable device 100 may also include a user interface 190 via which the wearer of the device may receive one or more recommendations or alerts generated from a remote server or other remote computing device, or from a processor within the device. The alerts could be any indication that can be noticed by the person wearing the wearable device. For example, the alert could include a visual component (e.g., textual or graphical information on a display), an auditory component (e.g., an alarm sound), and/or tactile component (e.g., a vibration). Further, the user interface 190 may include a display 192 where a visual indication of the alert or recommendation may be displayed. The display 192 may further be configured to provide an indication the battery status of the device or an indication of any measured physiological parameters, for instance, the GSR being measured by the device.

Figure 2A:
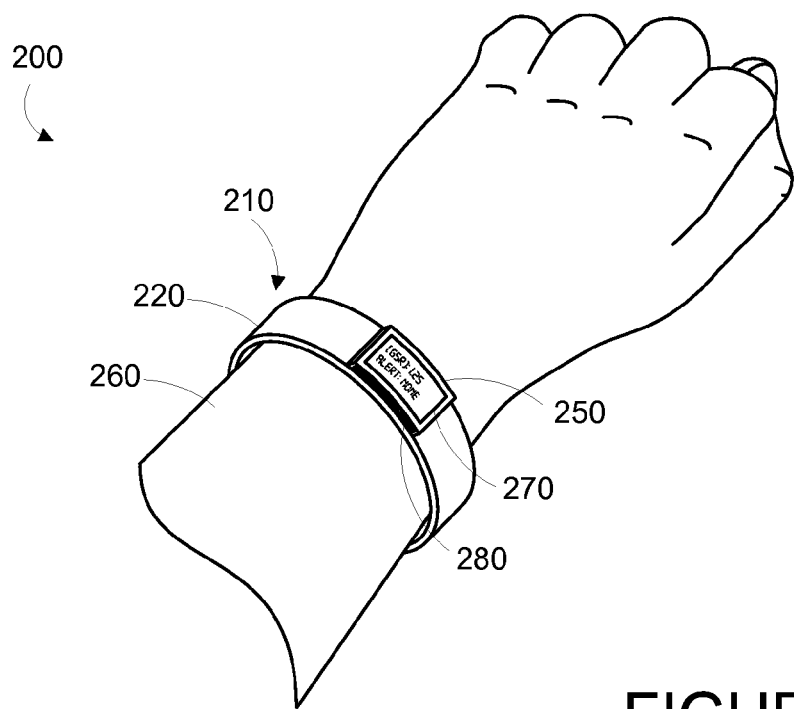
FIG. 2A is a perspective top view of an example wrist-mountable device, when mounted on a wearer's wrist.
Figure 2B:
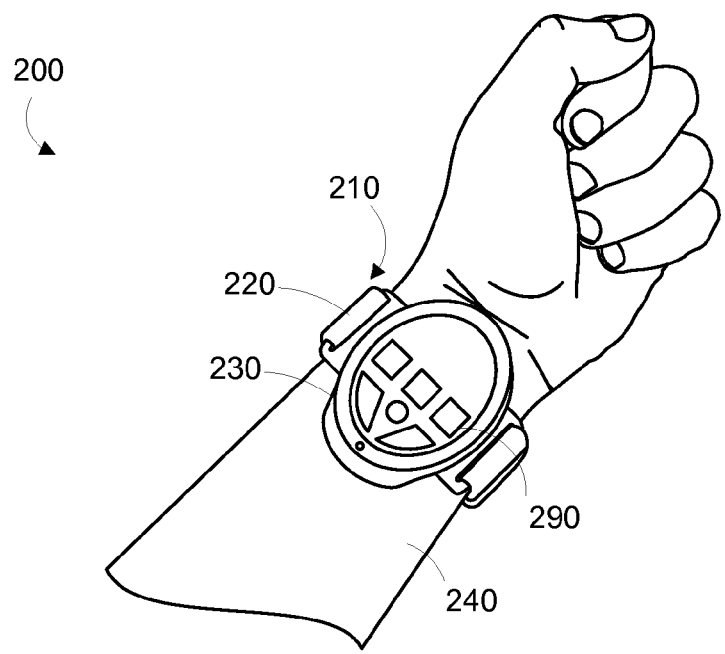
FIG. 2B is a perspective bottom view of the example wrist-mountable device shown in FIG. 2A, when mounted on a wearer's wrist.

In some examples, the wearable device is provided as a wrist-mounted device, as shown in FIGS. 2A, 2B, 3A-3C, 4A, 4B, 5 and 6. The wrist-mounted device may be mounted to the wrist of a living subject with a wristband or cuff, similar to a watch or bracelet. As shown in FIGS. 2A and 2B, the wrist mounted device 200 may include a mount 210 in the form of a wristband 220, a housing 230 positioned on the anterior side 240 of the wearer's wrist, and a user interface 250 positioned on the posterior side 260 of the wearer's wrist. The wearer of the device may receive, via the user interface 250, one or more recommendations or alerts generated either from a remote server or other remote computing device, or alerts generated by the operation of the wrist mounted device 200 (for example, alerts related to a GSR measured by the wrist mounted device 200). Such a configuration may be perceived as natural for the wearer of the device in that it is common for the posterior side 260 of the wrist to be observed, such as the act of checking a wrist-watch. Accordingly, the wearer may easily view a display 270 on the user interface. Further, the housing 230 may be located on the anterior side 240 of the wearer's wrist. However, other configurations are contemplated.

The display 270 may be configured to display a visual indication of the alert or recommendation and/or an indication of the status of the wearable device or an indication of measured physiological parameters, for instance, the GSR of the skin being measured by the wrist mounted device 200. Further, the user interface 250 may include one or more buttons 280 for accepting inputs from the wearer. For example, the buttons 280 may be configured to change the text or other information visible on the display 270. As shown in FIG. 2B, housing 230 may also include one or more buttons 290 for accepting inputs from the wearer. The buttons 290 may be configured to accept inputs for controlling aspects of the wrist mounted device 200, such as initiating a GSR measurement period, or inputs indicating the wearer's current health and/or affect state (i.e., normal, anxious, angry, calm, migraine, shortness of breath, heart attack, fever, "flu-like" symptoms, food poisoning, etc.).

Figure 3A:
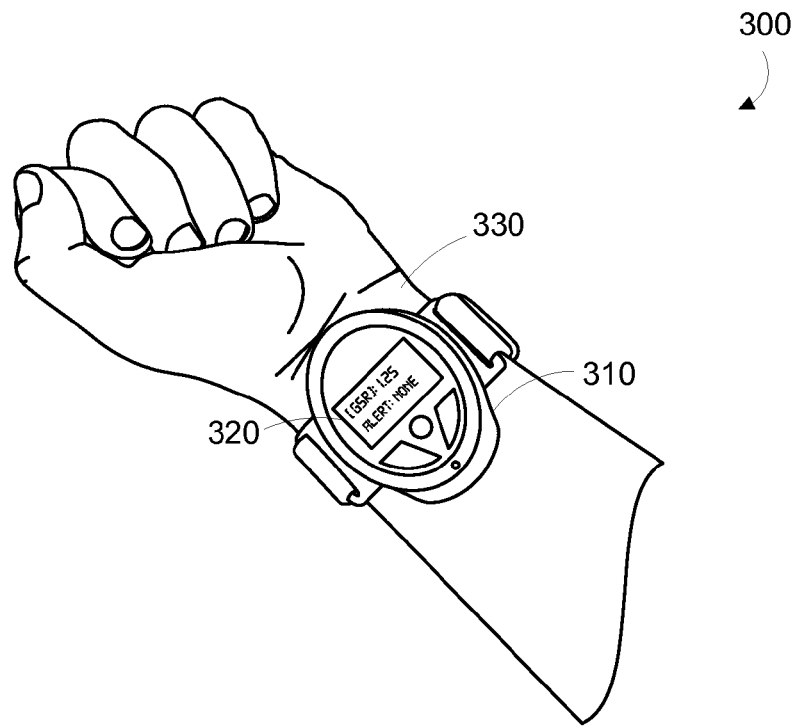
FIG. 3A is a perspective bottom view of an example wrist-mountable device, when mounted on a wearer's wrist.
Figure 3B:
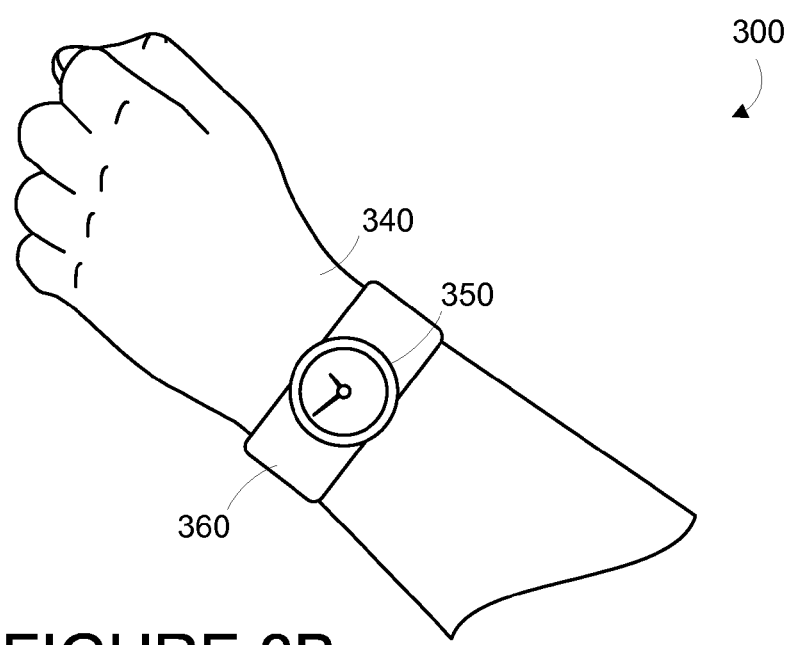
FIG. 3B is a perspective top view of the example wrist-mountable device shown in FIG. 3A, when mounted on a wearer's wrist.
Figure 3C:
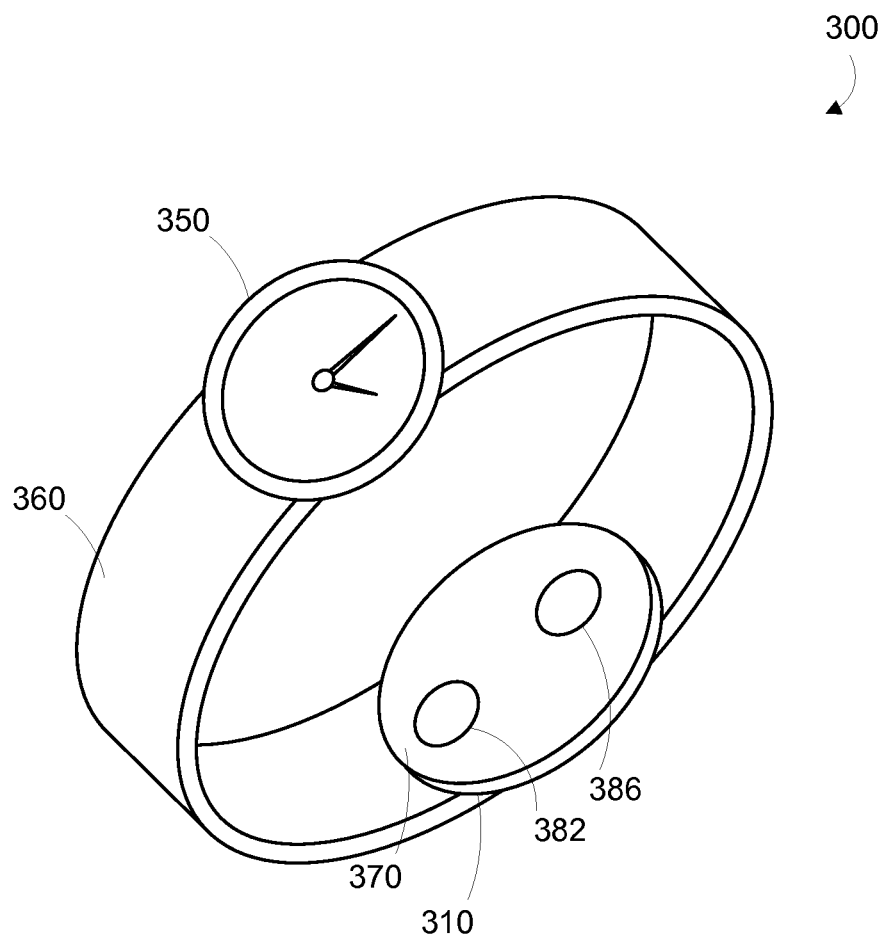
FIG. 3C is a perspective view of the example wrist-mountable device shown in FIGS. 3A and 3B.

In another example wrist-mounted device 300, shown in FIGS. 3A-3C, the housing 310 and user interface 320 are both provided on the same side of the wearer's wrist, in particular, the anterior side 330 of the wrist. On the posterior side 340, a watch face 350 may be disposed on the strap 360. While an analog watch is depicted in FIG. 3B, one of ordinary skill in the art will recognize that any type of clock may be provided, such as a digital clock.

As can be seen in FIG. 3C, the inner face 370 of the housing 310 is intended to be worn proximate to skin on an external surface of the wearer's body. A first electrical contact 382 and a second electrical contact 386 protrude from the inner face 370 of the housing 310 such that a measurement of the GSR of skin proximate to the inner face 370 could be measured using the electrical contacts 382, 386 when the wrist-mounted device 300 was mounted to a wrist of a wearer. The electrical contacts 382, 386 could also be used to charge a battery of the wrist-mounted device 300.

Figure 4A:
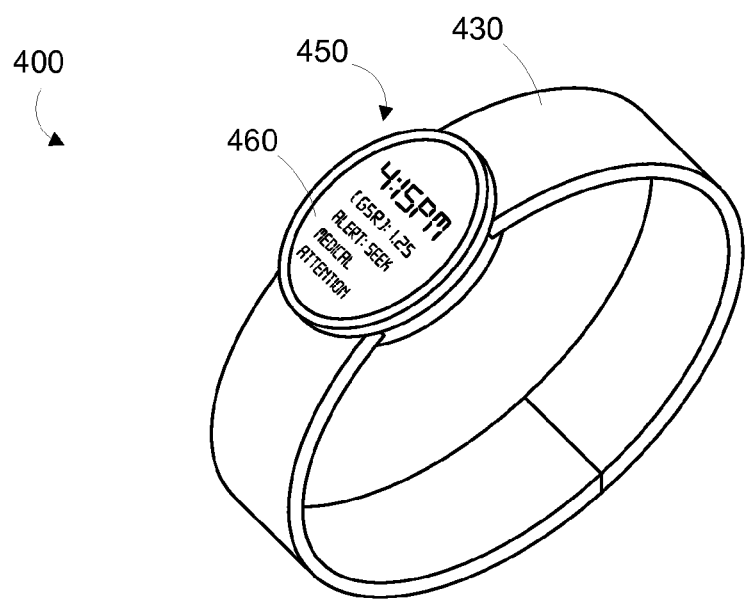
FIG. 4A is a perspective view of an example wrist-mountable device.
Figure 4B:
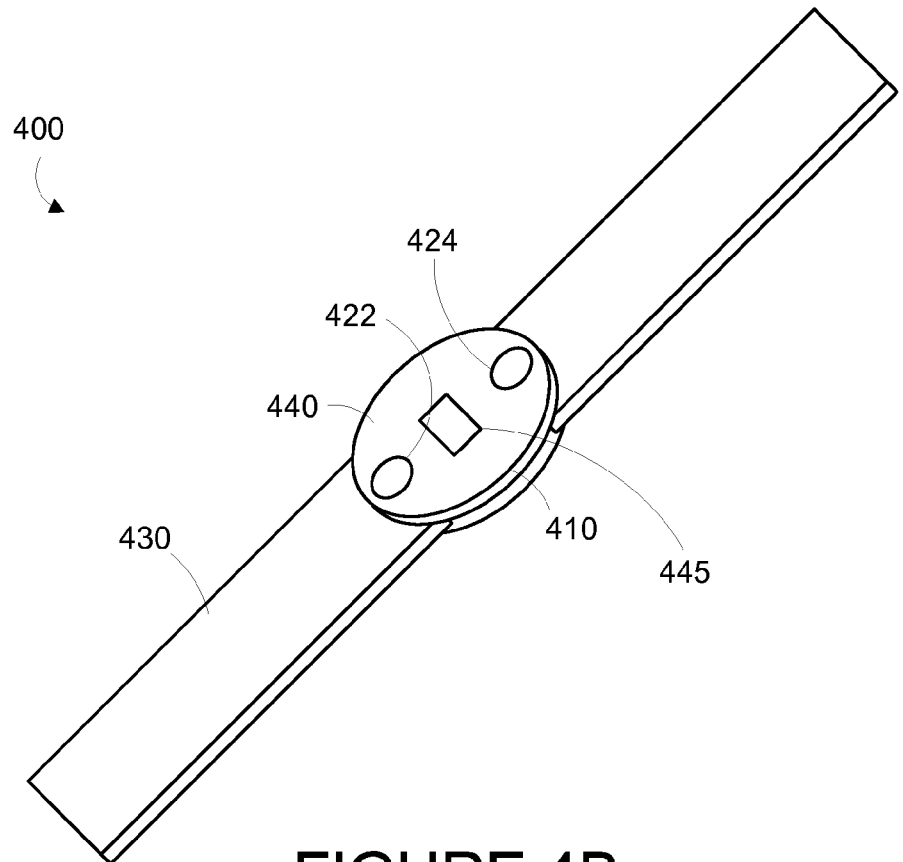
FIG. 4B is a perspective bottom view of the example wrist-mountable device shown in FIG. 4A.

In a further example shown in FIGS. 4A and 4B, a wrist mounted device 400 includes a housing 410, disposed on a strap 430. Inner face 440 of housing 410 may be positioned proximate to a body surface so that a first electrical contact 422 and a second electrical contact 424 protruding from the housing 410 may be used to measure the Galvanic skin resistance (GSR) of skin of the body surface proximate to the housing 410. A detector 445 for detecting at least one other physiological parameter of the wearer could also be disposed on the inner face 440 of the housing 410. A user interface 450 with a display 460 may be positioned facing outward from the housing 410. As described above in connection with other embodiments, user interface 450 may be configured to display data about the wrist mounted device 400, including whether the wrist mounted device 400 is active, a GSR of skin proximate to the inner face 440 of the housing 410 measured using the first and second electrical contacts 422, 424, physiological data about the wearer obtained using the detector 445, and one or more alerts generated by a remote server or other remote computing device, or a processor located on the wrist mounted device 400. The user interface 450 may also be configured to display the time of day, date, or other information that may be relevant to the wearer.

Figure 5:
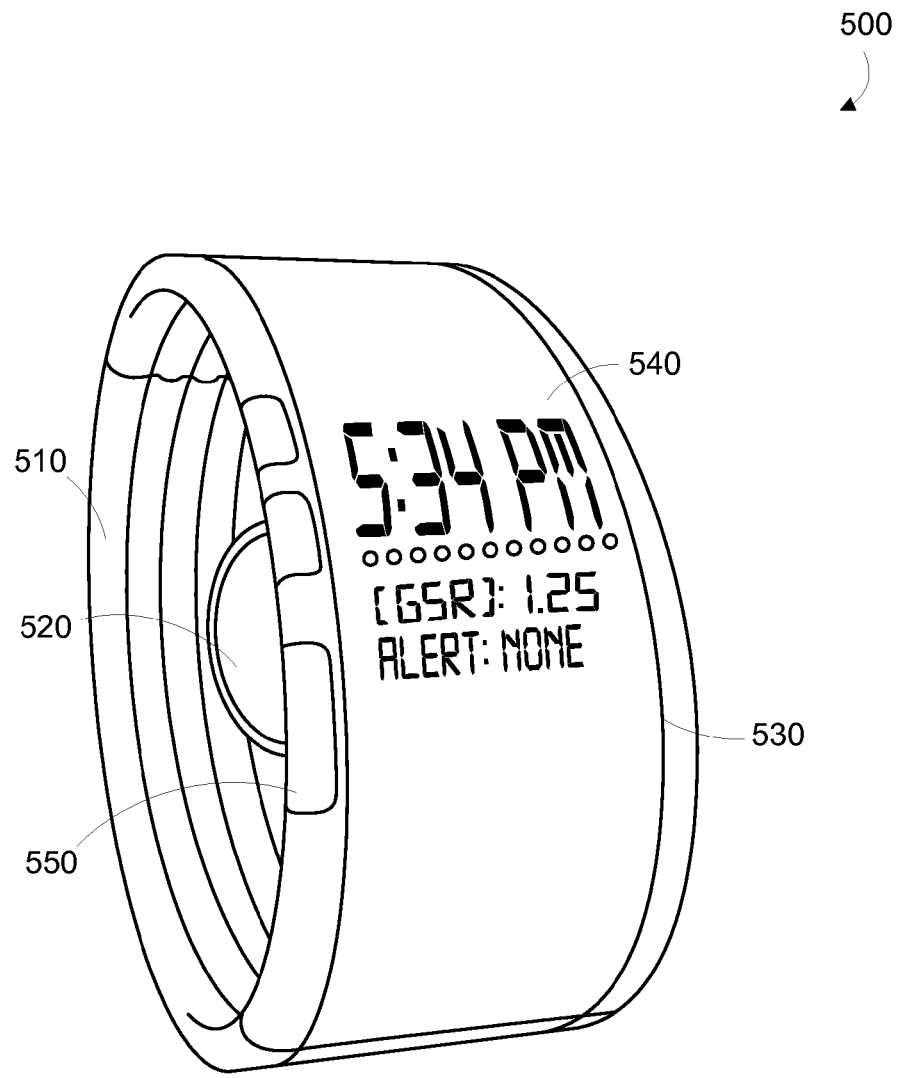
FIG. 5 is a perspective view of an example wrist-mountable device.
Figure 6:
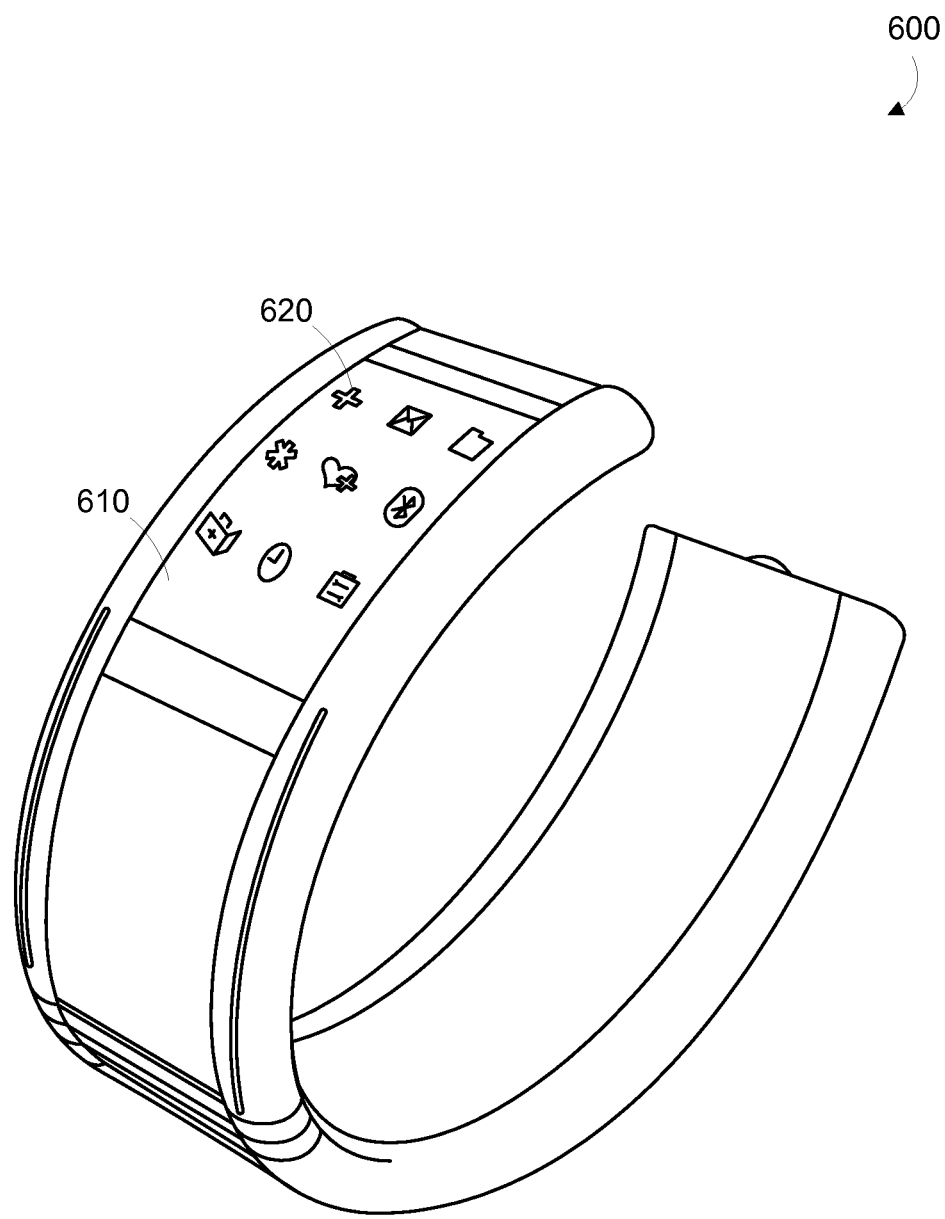
FIG. 6 is a perspective view of an example wrist-mountable device.

As shown in FIG. 5, in a further embodiment, wrist-mounted device 500 may be provided on a cuff 510. Similar to the previously discussed embodiments, device 500 includes a housing 520 and a user interface 530, which may include a display 540 and one or more buttons 550. The display 540 may further be a touch-screen display configured to accept one or more inputs by the wearer. For example, as shown in FIG. 6, display 610 may be a touch-screen configured to display one or more virtual buttons 620 for accepting one or more inputs for controlling certain functions or aspects of the device 600, or inputs of information by the user, such as current health and/or affect state.

Figure 7:
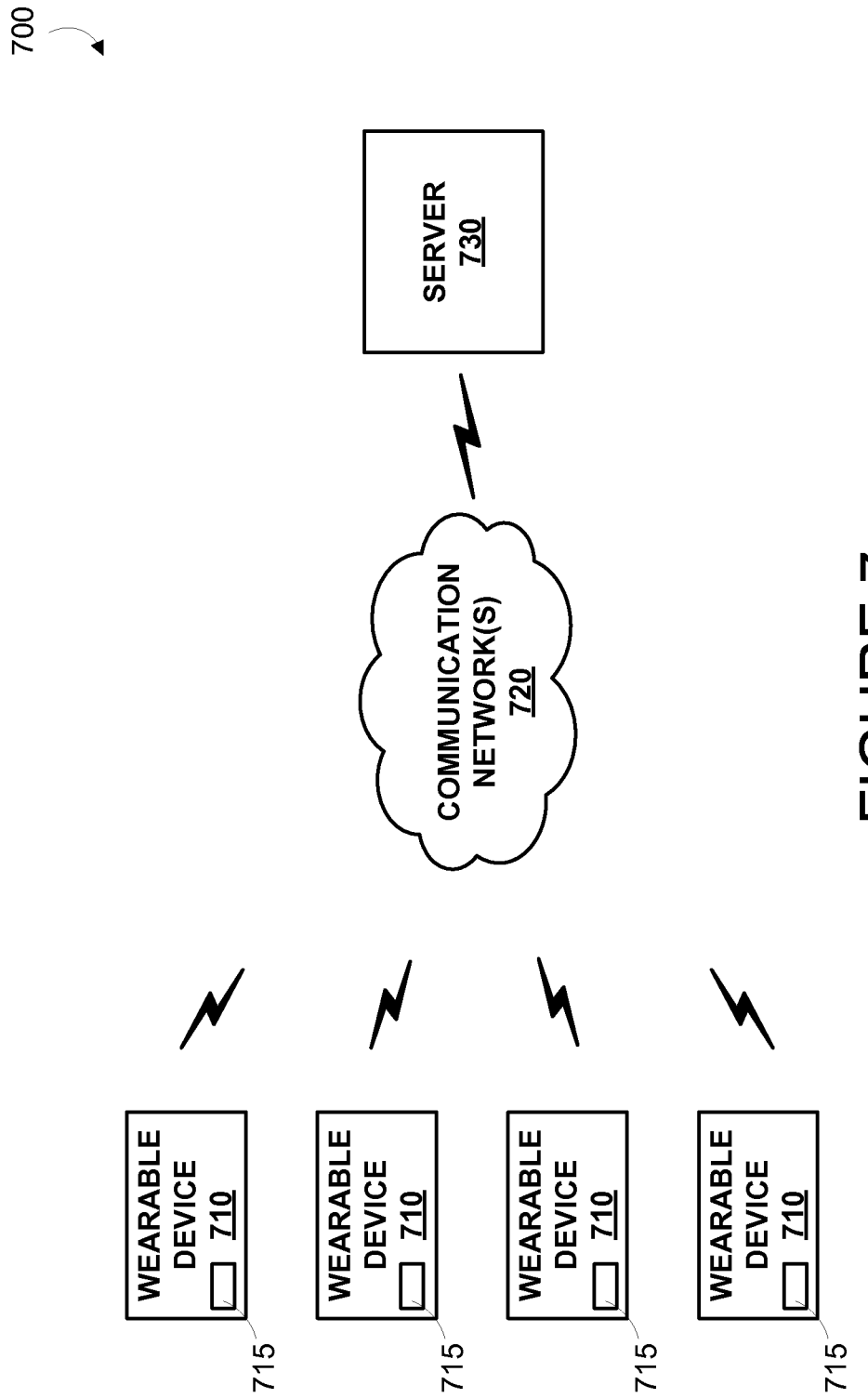
FIG. 7 is a block diagram of an example system that includes a plurality of wearable devices in communication with a server.

FIG. 7 is a simplified schematic of a system 700 including one or more wearable devices 710. The one or more wearable devices 710 may be configured to transmit data via a communication interface 715 over one or more communication networks 720 to a remote server 730. In one embodiment, the communication interface 715 includes a wireless transceiver for sending and receiving communications to and from the server 730. In further embodiments, the communication interface 715 may include any means for the transfer of data, including both wired and wireless communications. For example, the communication interface 715 may include a universal serial bus (USB) interface or a secure digital (SD) card interface. Communication networks 720 may include any of: a plain old telephone service (POTS) network, a cellular network, a fiber network and a data network. The server 730 may include any type of remote computing device or remote cloud computing network. Further, communication network 720 may include one or more intermediaries, including, for example wherein the wearable device 710 transmits data to a mobile phone or other personal computing device, which in turn transmits the data to the server 730.

In addition to receiving communications from the wearable device 710, such as data regarding health and/or affect state as input by the user or GSR measurements of skin of an external surface of the body of the wearer proximate to the wearable device, the server may also be configured to gather and/or receive either from the wearable device 710 or from some other source, information regarding a wearer's overall medical history, environmental factors and geographical data. For example, a user account may be established on the server for every wearer that contains the wearer's medical history. Moreover, in some examples, the server 730 may be configured to regularly receive information from sources of environmental data, such as viral illness or food poisoning outbreak data from the Centers for Disease Control (CDC) and weather, pollution and allergen data from the National Weather Service. Further, the server may be configured to receive data regarding a wearer's health state from a hospital or physician. Such information may be used in the server's decision-making process, such as recognizing correlations and in generating clinical protocols.

Additionally, the server may be configured to gather and/or receive the date, time of day and geographical location of each wearer of the device during each measurement period. If measuring physiological parameters of the user (e.g., GSR), such information may be used to detect and monitor spatial and temporal spreading of diseases. As such, the wearable device may be configured to determine and/or provide an indication of its own location. For example, a wearable device may include a GPS system so that it can include GPS location information (e.g., GPS coordinates) in a communication to the server. As another example, a wearable device may use a technique that involves triangulation (e.g., between base stations in a cellular network) to determine its location. Other location-determination techniques are also possible.

Further, some embodiments of the system may include privacy controls which may be automatically implemented or controlled by the wearer of the device. For example, where a wearer's collected data are uploaded to a cloud computing network for analysis by a clinician, the data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined.

Additionally or alternatively, wearers of a device may be provided with an opportunity to control whether or how the device collects information about the wearer (e.g., information about a user's medical history, social actions or activities, profession, a user's preferences, or a user's current location), or to control how such information may be used. Thus, the wearer may have control over how information is collected about him or her and used by a clinician or physician or other user of the data. For example, a wearer may elect that data, such as health state and physiological parameters, collected from his or her device may only be used for generating an individual baseline and recommendations in response to collection and comparison of his or her own data and may not be used in generating a population baseline or for use in population correlation studies.

III. Example Electronics Disposed in a Wearable Device

Figure 8:
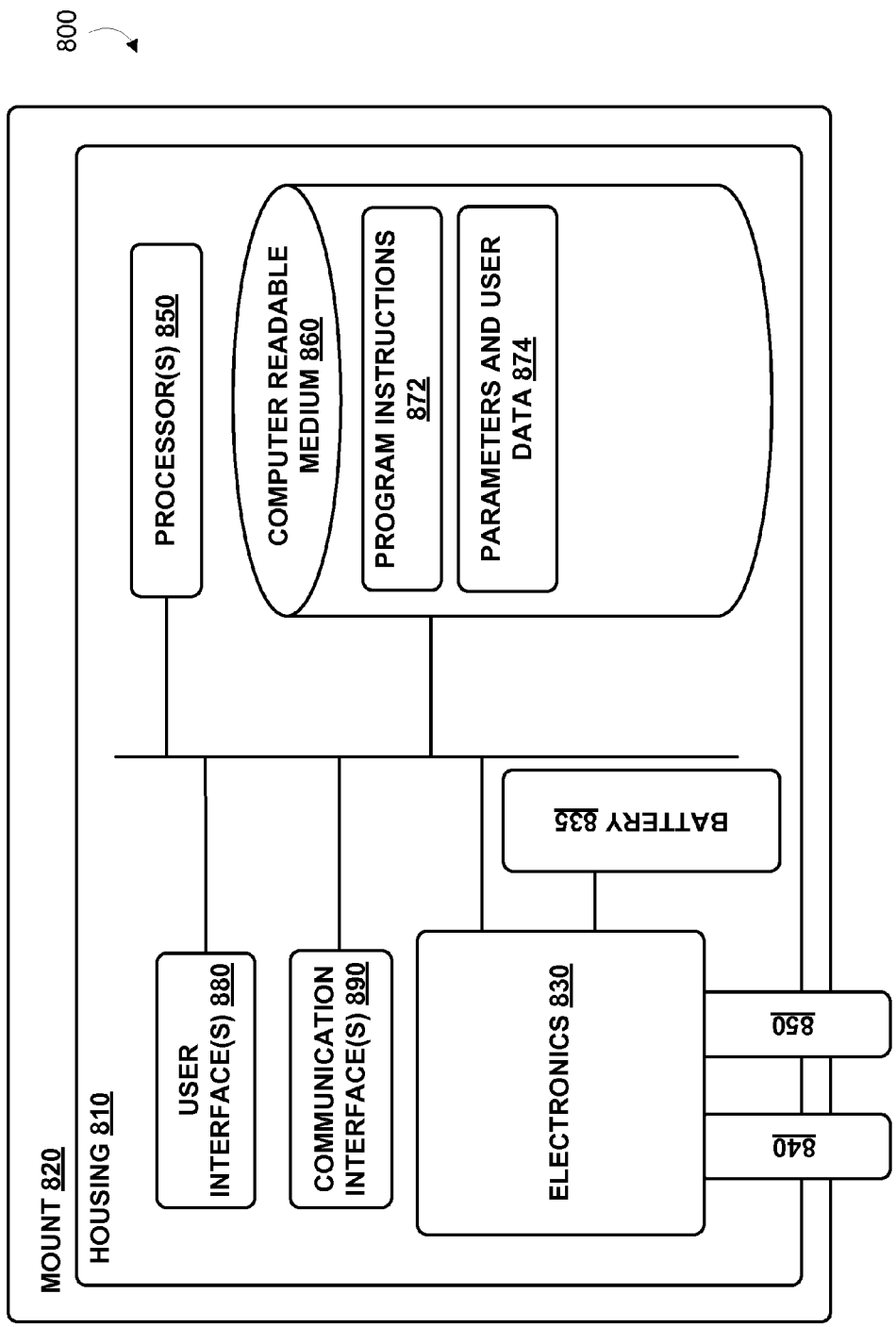
FIG. 8 is a functional block diagram of an example wearable device.

FIG. 8 is a simplified block diagram illustrating the components of a wearable device 800, according to an example embodiment. Wearable device 800 may take the form of or be similar to one of wearable device 100 and/or the wrist-mounted devices 200, 300, 400, 500, 600, shown in FIGS. 1, 2A-B, 3A-3C, 4A-4C, 5 and 6. However, wearable device 800 may also take other forms, for example, an ankle, waist, or chest-mounted device.

In particular, FIG. 8 shows an example of a wearable device 800 having a housing 810, electronics 830 for measuring a Galvanic skin response (GSR) of skin of an external surface of wearer proximate to the housing 810 and for recharging a rechargeable battery 835, a user interface 880, communication interface 890 for transmitting data to a server, and processor(s) 850. The components of the wearable device 800 may be disposed on a mount 820 for mounting the device to an external body surface where the GSR of the skin can be measured. The wearable device 800 also includes a first electrical contact 840 and a second electrical contact 850 protruding from the housing 810 and operatively coupled to the electronics 830. The electronics 830 use the first and second electrical contacts 840, 850 to measure the GSR of the skin proximate to the housing 810. Further, the electronics 830 use the first and second electrical contacts 840, 850 to interface with a charger or other external device or system to power the electronics and recharge the rechargeable battery 835.

Processor 850 may be a general-purpose processor or a special purpose processor (e.g., digital signal processors, application specific integrated circuits, etc.). The one or more processors 850 can be configured to execute computer-readable program instructions 872 that are stored in a computer readable medium 860 and are executable to provide the functionality of a wearable device 800 described herein.

The computer readable medium 860 may include or take the form of one or more non-transitory, computer-readable storage media that can be read or accessed by at least one processor 850. The one or more computer-readable storage media can include volatile and/or non-volatile storage components, such as optical, magnetic, organic or other memory or disc storage, which can be integrated in whole or in part with at least one of the one or more processors 850. In some embodiments, the computer readable medium 860 can be implemented using a single physical device (e.g., one optical, magnetic, organic or other memory or disc storage unit), while in other embodiments, the computer readable medium 860 can be implemented using two or more physical devices.

The electronics 830 could include a could include a GSR sensor. The GSR sensor could be configured to obtain a measurement relating to the GSR of the skin at the external body surface, via the first and second electrical contacts 840, 850, when a rectifier included in the electronics 830 is reverse biased. The GSR sensor could include a reference voltage source, a reference resistance, a voltage sensor, and/or other components in order to obtain a measurement relating to a GSR of skin of an external surface of a wearer using the electrical contacts 840, 580 when the housing 810 is mounted to the external surface of the wearer using the mount 820. The electronics 830 could be configured to measure the GSR of the skin by using the electrical contacts 840, 850 and the skin between them to form part of a resistive voltage divider, a Wheatstone bridge, or some other electronic network. A known voltage and/or current could then be applied to the resistive voltage divider, Wheatstone bridge or other electronic network such that a voltage, current or other sensor disposed as part of the electronics 830 could make a measurement that could be used to determine the GSR of the skin. The GSR sensor could additionally or alternatively include other components and/or configurations of components to obtain a measurement relating to the GSR of the skin. For example, the GSR sensor could include components configured to charge and/or discharge a capacitor at a rate related to the GSR of the skin. This rate could be measured (e.g., using a timer and a comparator, by repeatedly sampling the voltage across the capacitor, or some other method) to obtain a measurement relating to the GSR of the skin.

The electronics 830 could include a recharger configured to recharge the rechargeable battery 835 and to be powered through the electrical contacts 840, 850. In some examples, the wearable device 800 could be configured to be mounted on an external charger. The external charger could be configured to apply a voltage and/or current to the electrical contacts 840, 850 sufficient to power the recharger to recharge the rechargeable battery 835. The electronics 830 could include rectifiers or other elements disposed electrically between the recharger and the electrical contacts 840, 850. The rectifiers or other elements could be configured to reduce electrical interference in GSR measurements made using the electrical contacts 840, 850 when the wearable device 800 is mounted to an external surface of a wearer and not mounted to an external charger.

Additionally, the recharger could be configured for use without a rectifier. In particular, the recharger could be configured such that it does not source and/or sink a significant amount of current to/from the first electrical contact 840 when the recharger is not being powered through the first and second electrical contacts 850, 860. That way, the recharger may not interfere with use of the electrical contacts 850, 860 to obtain a measurement relating to the GSR of skin. For example, the recharger could be configured such that it does not source and/or sink a significant amount of current when the voltage between the first and second electrical contacts 850, 860 is below a charging threshold voltage, which could be higher than the reference voltage used for GSR measurement. Thus, voltages appearing between the first and second electrical contacts 850, 860 during use of the first and second electrical contacts 850, 860 to obtain a measurement relating to the GSR would be less than the charging threshold voltage, and the recharger would not source and/or sink an amount of current that would interfere with the measurement.

Note that, while the electronics 830, processor(s) 850, rechargeable battery 835, and other components are described herein as being disposed in a single housing 810, other configurations are anticipated. In some examples, a wearable device could include multiple housings (e.g., the wearable devices 100, 200, 300 illustrated in FIGS. 1, 2A-B, 3A-C) and the components of the wearable device could be distributed amongst the multiple housings. For example, a first housing could contain some of the electronics 830 (for example, GSR measurement electronics) and the electrical contacts 840, 580 could protrude from the first housing. A second housing could include the recharger electronics and the rechargeable battery 835 and elements disposed in the second housing could be electrically connected to elements disposed in the first housing. Other numbers of housings, configurations of housings, and dispositions of components within multiple housings are anticipated.

The program instructions 872 stored on the computer readable medium 860 may include instructions to perform or facilitate some or all of the device functionality described herein. For instance, program instructions 872 could include instructions to operate the electronics 830 to make a GSR measurement using the electrical contacts 840, 850. The program instructions 872 could include instructions to operate based on parameter and user data 874 stored in the computer readable medium 860 and/or modify the parameters and user data 874. For example, the parameters and user data 874 could include calibration data for the wearable device 800 and/or stored GSR measurements made using the wearable device 800.

The program instructions 872 stored on the computer readable medium 860 could include instructions for operating the electronics 830 to make a GSR measurement using the electrical contacts 840, 850. The instructions could include instructions to activate and/or set a value of a current source, a voltage source, a programmable resistor, an ADC and/or some other component(s) of the electronics 830. The instructions could include instructions to operate a voltage or current sensor to make a measurement relating to the GSR. The instructions could include instructions to determine a GSR based on the measurement. The instructions could further include instructions to determine the GSR based on calibration or other data stored in the parameters and user data 874. The instructions could include instructions to determine whether the wearable device 800 was mounted to skin on an external surface of a wearer based on the measurement relating to the GSR.

Other instructions in the program instructions 872 relating to the use of the electronics 830 to measure a GSR using the electrical contacts 840, 850 are anticipated. The program instructions 872 could include instructions to make a plurality of measurements and/or determinations of the GSR at a plurality of points in time using the electronics 830. The program instructions 872 could include instructions to store measurements of the GSR in the parameters and user data 874 and/or later or update calibration or other data in the parameters and user data 874 based on measurements of the GSR or other factors.

The program instructions 872 stored on the computer readable medium 860 could include instructions for operating the electronics 830 to recharge the rechargeable battery 835 and/or to power the wearable device 800 using the rechargeable battery 835. For example, the instructions could include instructions for operating switches or other electrical components to gate power from the electrical contacts 840, 850 to the recharger and/or from the recharger to the rechargeable battery 835. Additionally or alternatively, the instructions could include instructions to operate a voltage or current sensor (possibly the same sensor used to make GSR measurements) to detect the presence of an external charger in electrical contact with the electrical contacts 840, 850 and/or to detect a charge state of the rechargeable battery 835. The recharger and/or rectifier elements of the electronics 830 could be passive, that is, they could be configured to recharge the rechargeable battery 835 and/or power the wearable device 800 without direct operation by the processor(s) 850 or other elements of the wearable device 800 (other than the electrical contacts 840, 850) when the wearable device 800 is mounted to an external charger or other appropriately configured power source.

The program instructions 872 can include instructions for operating the user interface(s) 880. For example, the program instructions 872 could include instructions for displaying data about the wearable device 800, for displaying a measured and/or determined GSR or other information generated by the wearable device 800, or for displaying one or more alerts generated by the wearable device 800 and/or received from an external system. Further, program instructions 872 may include instructions to execute certain functions based on inputs accepted by the user interface(s) 880, such as inputs accepted by one or more buttons disposed on the user interface(s) 880.

Communication interface 890 may also be operated by instructions within the program instructions 872, such as instructions for sending and/or receiving information via an antenna, which may be disposed on or in the wearable device 800. The communication interface 890 can optionally include one or more oscillators, mixers, frequency injectors, etc. to modulate and/or demodulate information on a carrier frequency to be transmitted and/or received by the antenna. In some examples, the wearable device 800 is configured to indicate an output from the processor by modulating an impedance of the antenna in a manner that is perceivable by a remote server or other remote computing device.

In some examples, the communication interface(s) 890 could be operably coupled to the electrical contacts 840, 850 and could be configured to communicate with an external system by using the electrical contacts 840, 850. In some examples, this includes sending and/or receiving voltage and/or current signals transmitted through the electrical contacts 840, 580 when the wearable device 800 is mounted onto an external system such that the electrical contacts 840, 850 are in electrical contact with components of the external system.

In some examples, GSR measurements, wearer profiles, history of wearable device use, health state information input by device wearers and generated recommendations and clinical protocols may additionally be input to a cloud network and be made available for download by a wearer's physician. Trend and other analyses may also be performed on the collected data, such as physiological parameter data and health state information, in the cloud computing network and be made available for download by physicians or clinicians.

Further, GSR measurements and health state data from individuals or populations of device wearers may be used by physicians or clinicians in monitoring efficacy of a drug or other treatment. For example, high-density, real-time data may be collected from a population of device wearers who are participating in a clinical study to assess the safety and efficacy of a developmental drug or therapy. Such data may also be used on an individual level to assess a particular wearer's response to a drug or therapy. Based on this data, a physician or clinician may be able to tailor a drug treatment to suit an individual's needs.

In response to a determination by instructions contained in the program instructions 872 that a medical condition is indicated, the wearable device 800 may generate an alert via the user interface 880. The alert may include a visual component, such as textual or graphical information displayed on a display, an auditory component (e.g., an alarm sound), and/or tactile component (e.g., a vibration). The textual information may include one or more recommendations, such as a recommendation that the wearer of the device contact a medical professional, seek immediate medical attention, or administer a medication.

Figure 9:
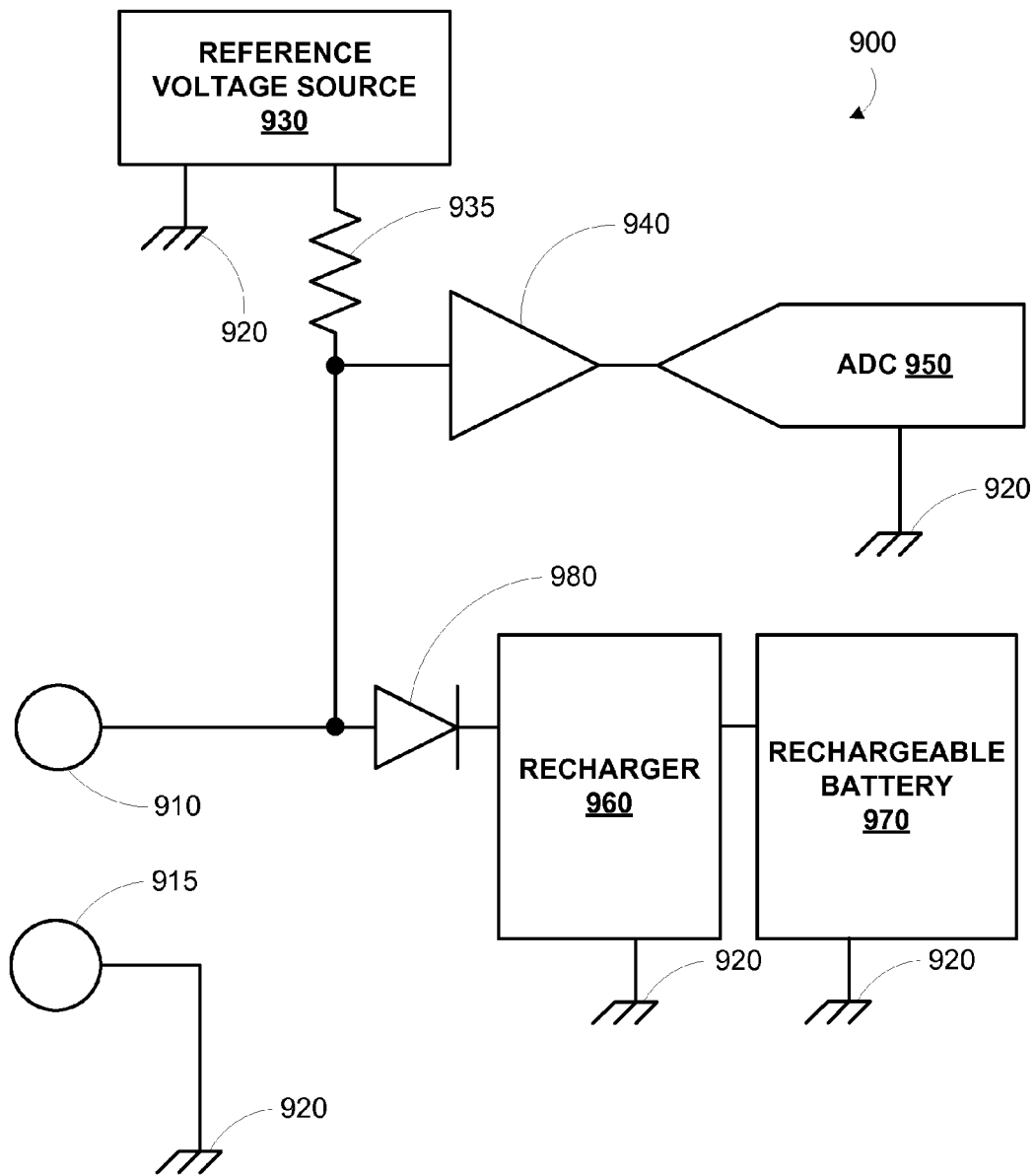
FIG. 9 is a functional block diagram of components disposed in an example wearable device.

FIG. 9 is a simplified circuit diagram of electronics 900 that could be disposed in a wearable device to measure a Galvanic skin response (GSR) and/or recharge a rechargeable battery 970 using a first electrical contact 910 and a second electrical contact 915 disposed in the wearable device. Electronics 900 are configured to include a common electrical ground 920 electrically connected to the second electrical contact 915. The electronics 900 include a GSR sensor configured to obtain a measurement relating to the GSR of skin proximate to the first and second electrical contacts 910, 915. The GSR sensor can include a reference voltage source 930, a resistor 935, and a voltage sensor that includes an amplifier 940 and an ADC 950. The electronics 900 also include a recharger 960 and a rectifier 980.

In the example of FIG. 9, the reference voltage source 930 is electrically connected to the first electrical contact 910 through the resistor 935. Additionally, the amplifier 940 has an input electrically connected to the first electrical contact 910 and an output connected to the ADC 950. The recharger 960 is electrically connected to the rechargeable battery 970. The recharger is also electrically connected to the first electrical contact 910 through the rectifier 980. The rectifier 980 is configured to be forward biased when the recharger is being powered through the first and second electrical contacts 910, 915; that is, the rectifier 980 is configured to substantially allow the passage of current through itself when current is flowing through the electrical contacts 910, 915 to power the recharger 960. Conversely, the rectifier 980 is configured to be reverse biased (i.e., to substantially not allow the passage of current through itself) when the recharger is not being powered through the first and second electrical contacts 910, 915. Further, at least the reference voltage source 930, ADC 950, recharger 960, and rechargeable battery 970 are electrically connected to the common electrical ground 920 that is electrically connected to the second electrical contact 915.

Electronics 900 could be disposed in a wearable device (e.g., the wearable devices 100, 200, 300, 400, 500, 600, 710, 800 illustrated in FIGS. 1, 2A-B, 3A-C, 4A-B, 5, 6, 7, and 8). Individual elements of the electronics 900 could be embodied as respective discrete components. Additionally or alternatively, one or more elements of the electronics 900 could be incorporated into one or more integrated circuits. In examples where the electronics 900 are included in a wearable device composed or multiple housings or other subassemblies, the elements of the electronics 900 could all be disposed in a single housing or subassembly or elements of the electronics 900 could be disposed in multiple housings or subassemblies and connected using wires, cables, or other means passing between housings or subassemblies.

The GSR sensor can include a voltage sensor coupled to the first electrical contact 910 and configured to measure a voltage between the first electrical contact 910 and the second electrical contact 915. Obtaining a measurement relating to the GSR of skin at an external body surface proximate to the first and second electrical contacts 910, 915 can include measuring the voltage between the first and second electrical contacts 910, 915. The voltage sensor includes an amplifier 940 and an analog-to-digital converter (ADC) 950. The use of an amplifier and ADC, as shown in FIG. 9, for a voltage sensor is meant as an example and not meant to be limiting. For example, the voltage sensor could include an ADC without an amplifier. Additionally or alternatively, the voltage sensor could include an ADC configured to include an amplifier, such that the voltage sensor included an amplifier and an ADC embodied in a single component. Other configurations of voltage sensor are also possible. Further, the GSR sensor could additionally or alternatively include other forms of sensor, including current sensors, voltage and/or current comparators, peak detectors, frequency counters, or other electronic sensing components and/or configurations of components.

The amplifier 940 could be any electronic component capable of amplifying a first voltage appearing at the first electrical contact 910 and generating a second voltage related to the first voltage. The amplifier 940 could be configured to have a gain (including a unity gain), a frequency response, an input impedance, an output impedance, and common-mode-rejection-ratio (CMRR), a power requirement, and/or other specifications according to an application. The amplifier 940 could include one or more transistors. For example, the amplifier could include a transistor configured as a common-source or common-emitter amplifier. The amplifier 940 could include multiple transistors, configured e.g. as a Darlington pair. The transistors could include bipolar junction transistors (BJTs), field-effect transistors (FETs), junction gate field-effects transistors (JFETs), and/or other types of transistors. The amplifier 940 could include one or more operational amplifiers. For example, the amplifier 940 could be an operational amplifier configured as a voltage follower. Other amplifier configurations are anticipated.

The ADC 950 could be part of a microcontroller disposed in a wearable device. The ADC 950 could be configured as a discrete component disposed in a wearable device. The ADC 950 could be operated by a microcontroller or other processor(s) to make a measurement of a voltage and/or current from the amplifier 940 (or, in embodiments lacking the amplifier 940, a voltage and/or current from the first electrical contact 910). The ADC 950 could be a direct-conversion ADC, a successive-approximation ADC, a sigma-delta ADC, or some other type of ADC. The ADC 950 could include an amplifier, a filter, a sample-and-hold, and/or some other components.

The voltage sensor could be used to measure a voltage relating to a GSR of skin proximate to the electrical contacts 910, 915. The voltage sensor could also be used to detect other signals. In some examples, the voltage sensor could be used to detect whether the electrical contacts 910, 915 are in contact with skin proximate to the electrical contacts 910, 915. Additionally or alternatively, the voltage sensor could be used to detect when an external charger or other power source was connected to the first and second electrical contacts 910, 915 and/or a charge state of the rechargeable battery 970. Other uses of the voltage sensor are anticipated.

The GSR sensor could include additional and/or alternate circuitry than that disclosed above. For example, the GSR sensor could include one or more comparators instead of or in addition to an ADC. The GSR sensor could include linear and nonlinear filtering circuitry and/or voltage isolation circuitry. The GSR sensor could include one or more analog components or functional blocks. The GSR sensor could include analog electronics to perform some analog calculation and/or filtering based on a measured voltage or other signal; the results of this analog calculation and/or filtering could be used to perform some function or could be digitized for use by a processor or microcontroller. For example, the GSR sensor could include analog circuitry to remove a DC offset from a measured voltage and could include a comparator to indicate when the measured voltage (without the DC offset) increased above a threshold value.

The reference voltage source 930 could be any component configured to provide a stable, specified reference voltage relative to a common electrical ground 920. For example, the reference voltage source 930 could include a forward or reverse biased Zener diode, germanium diode, silicon diode, and/or avalanche diode. The reference voltage source 930 could additionally or alternatively include a bandgap voltage reference. The reference voltage source 930 could be temperature stabilized. In some examples, a voltage provided by the reference voltage source could be adjustable, for example by a microcontroller connected to the reference voltage source.

The resistor 935 could be any electronic component having a stable reference resistance value. For example, the resistor could be a thin-film resistor, a thick-film resistor, a laser-trimmed resistor, a wire-wound resistor, or some other type of resistive element. In some examples, the resistor 935 could have an adjustable resistance, and the adjustable resistance could be controlled by e.g. a microcontroller. In some examples, the resistor 935 could have a reference resistance equal to between 1 megaohm and 10 megaohms. For example, the resistor 935 could have a reference resistance of 4 megaohms. In examples where the resistor 935 has a fixed reference resistance, the resistor 935 could be designed to have a known reference resistance. Additionally or alternatively, a reference resistance of the resistor 935 could be determined through calibration or some other method. The determined reference resistance could be stored in a memory accessible to a processor or other system configured to use the electronics 900 to measure the GSR of skin proximate to the electrical contacts 910, 915.

A voltage between the first electrical contact 910 and the second electrical contact 915 sensed by the voltage sensor could be related to a GSR of skin proximate to the electrical contacts 910, 915 when a wearable device including the electronics 900 is mounted on an external body surface of a wearer. For example, the sensed voltage could be a fraction of the reference voltage provided by the reference voltage source 930. The resistor 935 and the GSR of the skin proximate to the electrical contacts 910, 915 could act as a voltage divider. As such, the fraction of the reference voltage could correspond to the GSR of the skin divided by a sum of the GSR and the reference resistance of the resistor 935.

A processor or other system having access to a voltage measured by the voltage sensor could make a determination of the GSR. A processor or other system could make such a determination by determining a multiple of the reference resistance of the resistor 935. The multiple of the reference resistance could correspond to the measured voltage divided by a difference, where the difference corresponds to the measured voltage subtracted from the reference voltage provided by the reference voltage source 930. This determination could be represented by $R_{GSR}=R_{REF}*(V_{SENS}/(V_{REF}-V_{SENS}))$, where $R_{GSR}$ is the determined GSR, $R_{REF}$ is the reference resistance of the resistor 935, $V_{SENS}$ is the measured voltage, and $V_{REF}$ is reference voltage.

The processor or other system could additionally or alternatively use the measured voltage to determine whether the electrical contacts 910, 915 are in contact with skin, and/or whether the wearable contacts 910, 915 could be used to make a determination of the GSR of skin proximate to the electrical contacts 910, 915. For example, if the measured voltage was a sufficiently high fraction of the reference voltage, it could be determined that the electrical contacts 910, 915 are not in contact with skin and/or that the GSR of the skin was too large to be accurately determined using the electrical contacts 910, 915 and the electronics 900.

Obtaining a measurement relating to the GSR of skin using the electrical contacts 910, 915 could be affected by the recharger 960, rectifier 980, and/or rechargeable battery 970. In some examples, when a wearable device including the electronics 900 is mounted to an external surface of a wearer, a leakage current could flow from the recharger 960 through the reverse-biased rectifier 980 to the first electrical contact 910 and from there through the skin. As a result, the measurement obtained by the GSR sensor would be based on the leakage current in addition to the GSR of the skin among other factors relating to the configuration of the GSR sensor (e.g., the reference resistance of the resistor 935, and the reference voltage provided by the reference voltage source 930).

In examples where the obtained measurement is affected by a leakage current, determining a GSR based on the obtained measurement could be accomplished in a variety of ways. In some examples, determining a GSR based on the obtained measurement could be accomplished by adding or subtracting an offset to the obtained measurement. Additionally or alternatively, a more complicated model of the circuit, taking into account the effects of the leakage current, could be used to determine a GSR from the obtained measurement. Additionally or alternatively, a look-up table (LUT) could be used to determine a GSR from an obtained measurement. The LUT could be determined through experiment and/or using models of the electronics 900 or other related systems. In examples where the GSR is determined using a processor (e.g., processor(s) 850 of wearable device 800 in FIG. 8), information about the LUT could be stored in data storage that is accessible to the processor (e.g., in the parameters and user data 874 stored in the computer readable medium 860 in FIG. 8). Other methods for determining a GSR from an obtained measurement in scenarios including a leakage current are anticipated.

The reference voltage source 930 could be configured to be switched; that is, the reference voltage source 930 could be configured such that a processor or other system (not shown) could control the reference voltage source 930 to electrically connect the resistor 935 to a reference voltage, the common electrical ground 920, some other voltage, and/or to substantially disconnect the resistor 935 from any voltage (i.e., to connect the resistor 935 to a relatively high impedance). In some examples, the resistor 935 could be disconnected and/or connected to the common electrical ground to conserve power. In some examples, the reference voltage source 930 could switch repeatedly over time. For example, the reference voltage source 930 could switch between a reference voltage and the common electrical ground 920 at a specified frequency. The GSR could then be determined as a function of frequency by making a plurality of voltage measurements at a higher frequency than the frequency that the reference voltage source 930 was switched. Other methods and applications of switching the reference voltage source 930 are anticipated.

The recharger 960 could be configured to recharge a rechargeable battery 970 according to the requirements of the rechargeable battery 970. For example, the recharger 960 could be configured to operate in a constant current mode, applying power to recharge the rechargeable battery 970 at a varying voltage but at a specified constant current. Additionally or alternatively, the recharger 960 could be configured to operate in a constant voltage mode, applying power to recharge the rechargeable battery 970 at a varying current but at a specified voltage. The recharger 960 could be configured to operate in more than one mode according to a state of the rechargeable battery 970 and/or a state of a wearable device that includes the electronics 900. For example, the rechargeable battery 970 could be a lithium polymer battery, and the recharger 960 could be configured to begin recharging in a constant-current mode until the voltage of the rechargeable battery 970 reached a voltage threshold. Once the voltage of the rechargeable battery 970 reached the voltage threshold, the recharger 970 could begin charging in a constant-voltage mode until the charge current fell below a current threshold.

The recharger 960 could include transistors, inductors, switching power convertors, or other components. The recharger 960 could provide status information to other systems. For example, the recharger 960 could provide a charge status indicating that the rechargeable battery 970 was fully charged. The recharger 960 could be configured to operate under the control of another system. For example, a processor could control the recharger 960 to reduce a charging current if the processor determined that the electrical contacts 910, 915 were electrically connected to a low-capacity external charging system. Other configurations and applications of the recharger 960 are anticipated.

The rechargeable battery 970 could be any component capable of powering the electronics 900 and/or a wearable device including the electronics 900 and capable of being recharged by the recharger. The rechargeable battery could have a variety of chemistries, including nickel-metal-hydride, lithium polymer, zinc-polymer, nickel-cadmium, or other rechargeable battery chemistries. The rechargeable battery 970 could include a supercapacitor or other energy storage elements. The rechargeable battery 970 could include a single cell or more than one cell configured in series or in parallel. In examples where the rechargeable battery 970 includes multiple cells, the rechargeable battery 970, recharger 960, and/or other systems may be configured to recharge, discharge, or otherwise interact with individual cells of the rechargeable battery 970 independently of other cells of the rechargeable battery 970.

The rectifier 980 could be any electronic component capable of being configured such that the rectifier 980 substantially allows the flow of current from the first electrical contact 910 to the recharger 960 (i.e., the rectifier 980 is forward biased) when the recharger 960 is being powered through the electrical contacts 910, 915 (e.g., when an external charger or other system is electrically connected to the electrical contacts 910, 915 and providing power through the electrical contacts 910, 915). Further, the rectifier 980 is configured such that it allows substantially no current to flow through itself to/from the first electrical contact 910 from/to the recharger 960 (i.e., the rectifier 980 is reverse biased) when recharger 960 is not being powered through the electrical contacts 910, 915. The rectifier 980 could be a discrete component or it could be included as part of the recharger 960 and/or some other integrated circuit(s).

In some examples, the rectifier 980 includes a diode. For example, the rectifier 980 could be a silicon diode, a germanium diode, an avalanche diode, a Schottky diode, a PIN diode, a Zener diode, or some other type of diode. In some examples, the rectifier 980 includes one or more transistors. For example, the rectifier 980 could include bipolar junction transistor(s) (BJTs), field-effect transistor(s) (FETs), junction gate field-effects transistor(s) (JFETs), and/or other types of transistors. The rectifier 980 could be configured to operate without outside control by a processor or other system and/or could be configured to be switched or otherwise controlled by a processor or other system. In some examples, the rectifier 980 could include an electronic switch (for example, a FET) controlled by the recharger 960, a processor, or some other system. For example, a processor could determine that a charger or other power source was electrically connected to the electrical contacts 910, 915 (e.g., by sensing a voltage between the electrical contacts 910, 915 using the voltage sensor). In response to this determination, the processor could operate the rectifier 980 to conduct current from the first electrical contact 910 to the recharger 960. Otherwise, the processor could operate the rectifier to not conduct current.

Alternatively, the recharger 960 could be configured such that the rectifier 980 is omitted. In particular, the recharger 960 could be configured such that it does not source and/or sink a significant amount of current to/from the first electrical contact 910 when the recharger is not being powered through the first and second electrical contacts 910, 915 and, thus, not interfere with use of the electrical contacts 910, 915 to obtain a measurement relating to the GSR of skin. For example, the recharger 960 could be configured such that it did not source and/or sink a significant amount of current when the voltage between the first and second electrical contacts 910, 915 is below a charging threshold voltage, which is higher than the reference voltage provided by the reference voltage source 930. Thus, voltages appearing between the first and second electrical contacts 910, 915 during use of the first and second electrical contacts 910, 915 to obtain a measurement relating to the GSR would be less than the charging threshold voltage.

The electronics 900 could be configured and/or could include additional components to perform additional functions to those described above. In some examples, the GSR sensor could be operated to determine a type and/or capacity of a charger electrically connected to the electrical contacts. In some examples, the GSR sensor could be operated to receive communications from an external device that is configured to be connected to the electrical contacts 910, 915 and to transmit information to the electronics 900 by modulating a voltage waveform presented to the electrical contacts 910, 915. In some examples, the electronics 900 could be configured to measure other physiological properties of a wearer of a device including the electronics 900. For example, the GSR sensor could be configured to sense a Galvanic skin potential, and electrocardiogram (ECG), an electromyogram (EMG), and/or other signals and/or properties of a wearer by using the electrical contacts 910, 915. Other configurations and applications of the electronics 900 and of wearable devices or other systems including the electronics 900 are anticipated.

IV. Illustrative Methods for Operating a Wearable Device

Figure 10:
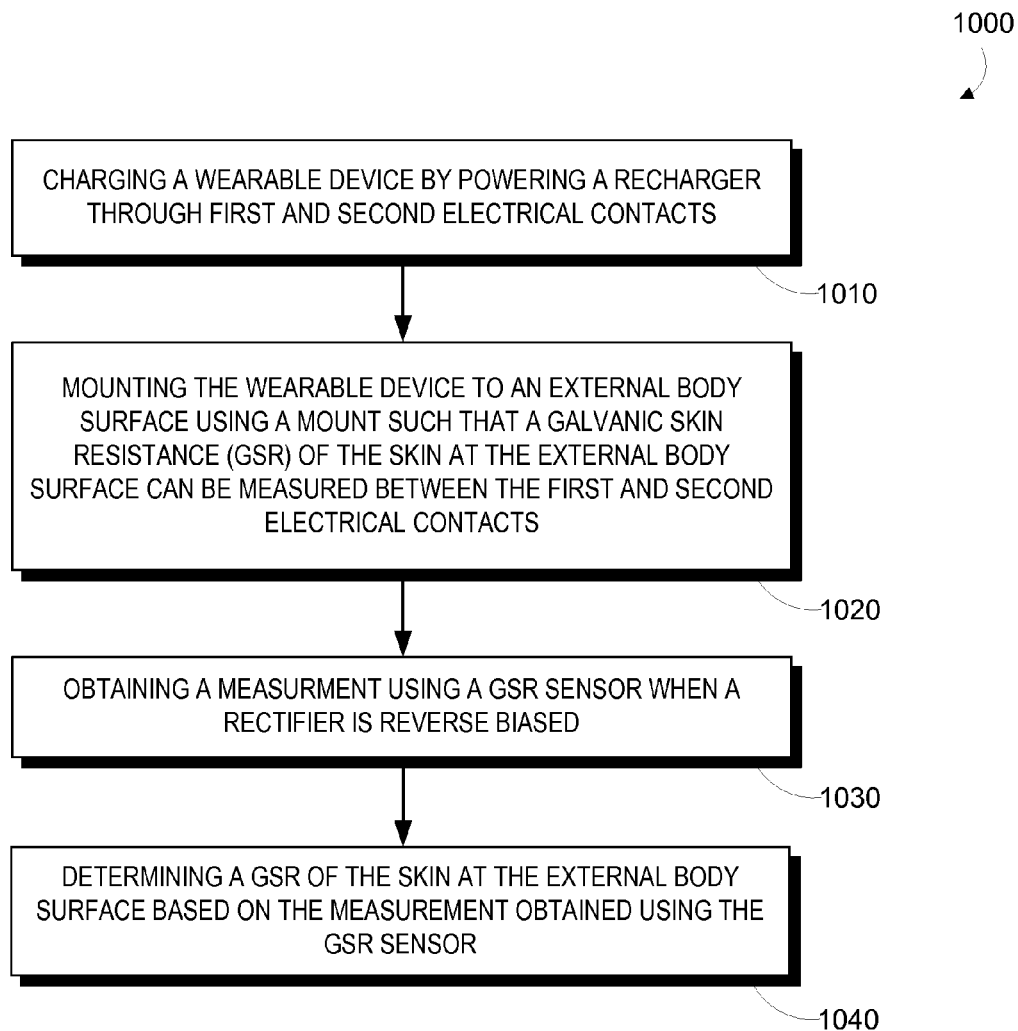
FIG. 10 is a flowchart of an example method.

FIG. 10 is a flowchart of a method 1000 for operating a wearable device. The operated wearable device includes (i) a housing, (ii) a rechargeable battery in the wearable device, (iii) a mount configured to mount the housing to an external body surface, (iv) first and second electrical contacts protruding from the housing, (v) a GSR sensor configured to obtain a measurement relating to a GSR of skin via the first and second electrical contacts, (vi) a recharger configured to recharge the rechargeable battery and to be powered through the first and second electrical contacts, and (vii) a rectifier connected between the recharger and the first electrical contact. The rectifier could be configured to be forward biased when the recharger is being powered through the first and second electrical contacts and reverse biased when the charger is not being powered through the first and second electrical contacts.

The method 1000 includes charging the wearable device by powering the recharger through the first and second electrical contacts (1010). For example, the wearable device could be placed on or in an external charging device. The external charging device could include two charging points configured to make electrical contact with the first and second electrical contacts of the wearable device when the wearable device was placed in or on the external charging device.

The external charging device could provide a voltage and/or current through the charging points to a wearable device placed in or on the external charging device. Elements of the wearable device could be operated based on the placement of the wearable device in or on the external charging device. For example, the rectifier could be operated to allow a powering current from the eternal charging device through the first electrical contact and through the rectifier to the recharger, such that the recharger could be powered by the powering current and could recharge the rechargeable battery.

The method 1000 further includes mounting the wearable device to an external body surface using the mount such that a Galvanic skin resistance (GSR) of the skin at the external body surface can be measured between the first and second electrical contacts (1020). For example. In some examples, the wearable device could be configured to be mounted to a wrist of a wearer (e.g., the embodiments illustrated in FIGS. 1, 2A-B, 3A-C, 4A-B, 5, and 6) such that the first and second electrical contacts were in contact with skin of the wrist of the wearer. In some examples, the mount includes an adhesive, and mounting the wearable device to an external body surface (1020) includes activating, applying, and/or exposing the adhesive and adhering the wearable device to the external body surface.

The method 1000 also includes obtaining a measurement using the GSR sensor when the rectifier is reverse biased (1030). For example, the GSR sensor could include a reference voltage source configured to provide a reference voltage relative to the second electrical contact, a resistor having a reference resistance and connected between the reference voltage source and the first electrical contact, and a voltage sensor coupled to the first electrical contact. Obtaining a measurement using the GSR sensor when the rectifier is reverse biased could include using a processor or other device disposed in the wearable device using operate the voltage sensor to measure the voltage between the first electrical contact and the second electrical contact. The measured voltage could be related to the reference voltage, the reference resistance, and the GSR of the skin at the external body surface. For example, the measured voltage could be a fraction of the reference voltage, wherein the fraction corresponds to the GSR of the skin divided by a sum of the GSR of the skin and the reference resistance.

Measuring a voltage using the voltage sensor (1030) could additionally include using the voltage sensor to measure a plurality of voltages at a plurality of points in time. For example, a wearable device could be configured to periodically measure a voltage using the voltage sensor (1030) at a specified frequency. Additionally or alternatively, the wearable device could be configured to measure a voltage using the voltage sensor (1030) a plurality of times based on a command received from an external system in communication with the wearable device, a command input by a user of the wearable device, and/or a determination made by components (e.g., a processor) of the wearable device.

The method 1000 also includes determining a Galvanic skin resistance (GSR) of the skin at the external body surface based on the measurement obtained using the GSR sensor (1040). In some examples, a processor or other system disposed in the wearable device could operate a voltage sensor included in the GSR sensor to measure the voltage between the first electrical contact and the second electrical contact. The processor could then execute instructions such that a GSR of the skin was determined based at least on the measured voltage. Determining the GSR of the skin at the external body surface based on the measurement obtained using the GSR sensor could include determining a multiple of a reference resistance of a resistor. The determined multiple could correspond to the measured voltage divided by a difference, wherein the difference corresponds to the measured voltage subtracted from a reference voltage of a reference voltage source. This determination could be represented by $R_{GSR}=R_{REF}*(V_{SENS}/(V_{REF}-V_{SENS}))$, where $R_{GSR}$ is the determined GSR, $R_{REF}$ is the reference resistance of the resistor, $V_{SENS}$ is the measured voltage, and $V_{REF}$ is reference voltage. Other methods of determining the GSR of the skin based voltage measured using the voltage sensor are anticipated. In some examples, determining the GSR of the skin could include determining a leakage current through the rectifier.

The method 1000 for operating a wearable device could include additional steps relating to a determined GSR of the skin at the external body surface. In some examples, the method 1000 could include indicating the determined GSR using a display disposed in the wearable device. In some examples, the method 1000 could include wirelessly indicating the determined GSR using a wireless transmitter disposed in the wearable device. For example, the wearable device could indicate a determined GSR or sequence of GSRs to a remote system (e.g., a server or cloud service accessible to a healthcare provider). In some examples, the method 1000 could include operating the wearable device based on the determined GSR. For example, the wearable device could be operated to generate an alert, send a transmission to a remote system, or some other action in response to a determined GSR or sequence of determined GSRs (e.g., if the determined GSR exceeded a threshold). Other applications of a determined GSR are anticipated.

The example method 1000 illustrated in FIG. 10 is meant as an illustrative, non-limiting example. Additional or alternative elements of the method and additional or alternative components of the wearable device are anticipated, as will be obvious to one skilled in the art.

CONCLUSION

Where example embodiments involve information related to a person or a device of a person, the embodiments should be understood to include privacy controls. Such privacy controls include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

The particular arrangements shown in the Figures should not be viewed as limiting. It should be understood that other embodiments may include more or less of each element shown in a given Figure. Further, some of the illustrated elements may be combined or omitted. Yet further, an exemplary embodiment may include elements that are not illustrated in the Figures.

Additionally, while various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are contemplated herein.

What is claimed is:

1. A wearable device, comprising:
   a housing;
   a rechargeable battery;
   a mount configured to mount the housing to an external body surface;
   first and second electrical contacts protruding from the housing, wherein the first and second electrical contacts are configured to contact skin at the external body surface when the housing is mounted on the external body surface; and
   electronics, wherein the electronics comprises:
      a recharger configured to recharge the rechargeable battery, wherein the recharger is configured to be powered through the first and second electrical contacts; and
      a GSR sensor configured to obtain a measurement relating to a Galvanic skin resistance (GSR) of the skin at the external body surface via the first and second electrical contacts, when the recharger is not being powered through the first and second electrical contacts, wherein the GSR sensor comprises:
         a reference voltage source configured to provide a reference voltage relative to the second electrical contact;
         a resistor connected between the reference voltage source and the first electrical contact, wherein the resistor has a reference resistance; and
         a voltage sensor coupled to the first electrical contact, wherein the voltage sensor is configured to sense a voltage between the first and second electrical contacts, wherein the voltage is related to the reference voltage, the reference resistance, and the GSR of the skin at the external body surface.

2. The wearable device of claim 1, wherein the electronics further comprises:
   a rectifier connected between the recharger and the first electrical contact, wherein the rectifier is configured to be forward biased when the recharger is being powered through the first and second electrical contacts and to be reverse biased when the recharger is not being powered through the first and second electrical contacts,
   wherein the GSR sensor is configured to obtain the measurement relating to the GSR of the skin at the external body surface, via the first and second electrical contacts, when the rectifier is reverse biased.

3. The wearable device of claim 2, wherein the rectifier comprises a diode.

4. The wearable device of claim 2, wherein the rectifier comprises a transistor.

5. The wearable device of claim 1, wherein the voltage sensed by the voltage sensor when the housing is mounted on the external body surface is a fraction of the reference voltage, wherein the fraction corresponds to the GSR of the skin divided by a sum of the GSR of the skin and the reference resistance.

6. The wearable device of claim 1, further comprising a user interface configured to provide a user-discernible indication of the GSR.

7. The wearable device of claim 1, further comprising a wireless communication interface configured to transmit data indicative of the GSR.

8. The wearable device of claim 1, wherein the GSR sensor further comprises an amplifier and an analog-to-digital converter.

9. The wearable device of claim 1, wherein the external body surface is a wrist location.

10. The wearable device of claim 1, wherein the first and second electrical contacts are separated by a distance of between 1 millimeter and 50 millimeters.

11. The wearable device of claim 1, wherein the first and second electrical contacts are spring-loaded.

12. The wearable device of claim 1, wherein the housing is configured to be water-resistant, wherein the first and second electrical contacts are configured to protrude from the housing such that the housing is water-resistant.

13. A method, comprising:
   charging a wearable device via first and second electrical contacts protruding from a housing of the wearable device, wherein charging the wearable device comprises forward biasing a rectifier in the wearable device and powering a recharger in the wearable device through the forward biased rectifier, wherein the recharger is configured to recharge a rechargeable battery in the wearable device;
   mounting the wearable device to an external body surface such that the first and second electrical contacts contact skin at the external body surface; and
   obtaining, using a GSR sensor in the wearable device, a measurement relating to a Galvanic skin resistance (GSR) of the skin at the external body surface via the first and second electrical contacts while the rectifier is reverse biased, wherein the GSR sensor comprises a voltage sensor electrically connected to the first electrical contact and a reference voltage source electrically connected to the first electrical contact through a resistor having a reference resistance, wherein obtaining the measurement comprises:
   the reference voltage source generating a reference voltage relative to the second electrical contact, such that a fraction of the reference voltage appears across the first and second electrical contacts, the fraction being related to the GSR and the reference resistance; and the voltage sensor measuring a voltage between the first electrical contact and the second electrical contact, wherein the measured voltage corresponds to the fraction of the reference voltage.

14. The method of claim 13, wherein the wearable device comprises a processor, further comprising determining, using the processor, the GSR of the skin at the external body surface based on the measurement obtained using the GSR sensor.

15. The method of claim 14, wherein determining the GSR of the skin at the external body surface based on the measurement obtained using the GSR sensor comprises determining a multiple of the reference resistance, wherein the multiple corresponds to the measured voltage divided by a difference, wherein the difference corresponds to the measured voltage subtracted from the reference voltage.

16. The method of claim 14, further comprising indicating the determined GSR using a display disposed in the wearable device.

17. The method of claim 14, further comprising wirelessly indicating the determined GSR using a wireless transmitter disposed in the wearable device.

18. The method of claim 14, further comprising operating the wearable device based on the determined GSR.

* * * * *